United States Patent [19]

Deirmendjian et al.

[11] Patent Number: 5,891,073
[45] Date of Patent: Apr. 6, 1999

[54] ANKLE BRACE

[76] Inventors: Gary Kara Deirmendjian, 5/529-533 Church Street, North Parramatta NSW 2151; Eugene Sherry, 25 Ridge Street, Gordon, New South Wales 2072, both of Australia

[21] Appl. No.: 110,921

[22] Filed: Jul. 6, 1998

Related U.S. Application Data

[63] Continuation-in-part of Ser. No. 773,412, Dec. 27, 1996, abandoned.

[30] Foreign Application Priority Data

Aug. 2, 1996 [AU] Australia ................................ PO 1436

[51] Int. Cl.⁶ .......................................................... A61F 5/00
[52] U.S. Cl. .............................................. 602/27; 602/65
[58] Field of Search .................................. 602/5, 23, 24, 602/27–29, 60–62, 65, 66; 128/882

[56] References Cited

U.S. PATENT DOCUMENTS

| | | | |
|---|---|---|---|
| 3,407,811 | 10/1968 | Stubbs | 602/65 |
| 4,811,727 | 3/1989 | Etienne | 602/23 |
| 5,014,691 | 5/1991 | Cueman et al. | 602/27 |
| 5,050,620 | 9/1991 | Cooper | 602/27 |
| 5,067,486 | 11/1991 | Hely | 602/65 |
| 5,185,000 | 2/1993 | Brandt et al. | 602/65 X |
| 5,330,419 | 7/1994 | Toronto et al. | 602/27 |
| 5,613,941 | 3/1997 | Prengler | 602/27 X |

*Primary Examiner*—Linda C. M. Dvorak
*Attorney, Agent, or Firm*—Oppenheimer Wolff & Donnelly LLP

[57] ABSTRACT

An ankle brace comprising ankle anchor strap (7) adapted to attach to the ankle of a user above the ankle joint and a heel support (5) adapted to fit under and support the heel of the user. A first bracing strap (11) extends from a point at or adjacent to a rear portion of the heel support (5) to a point at or adjacent a front portion of the ankle anchor strap (7) when each is fitted to the foot of said user. A second bracing strap (11) extends from a point at or adjacent to a front portion of the heel support (5) to a point at or adjacent a rear portion of the ankle anchor strap (7) when each is fitted to the foot of said user said first and second bracing straps (11) extending around an outer side of the user's ankle in use and each adapted, in use, to apply a tensile force to the heel support (5) so as to seek to raise the outer side of the user's heel.

15 Claims, 7 Drawing Sheets

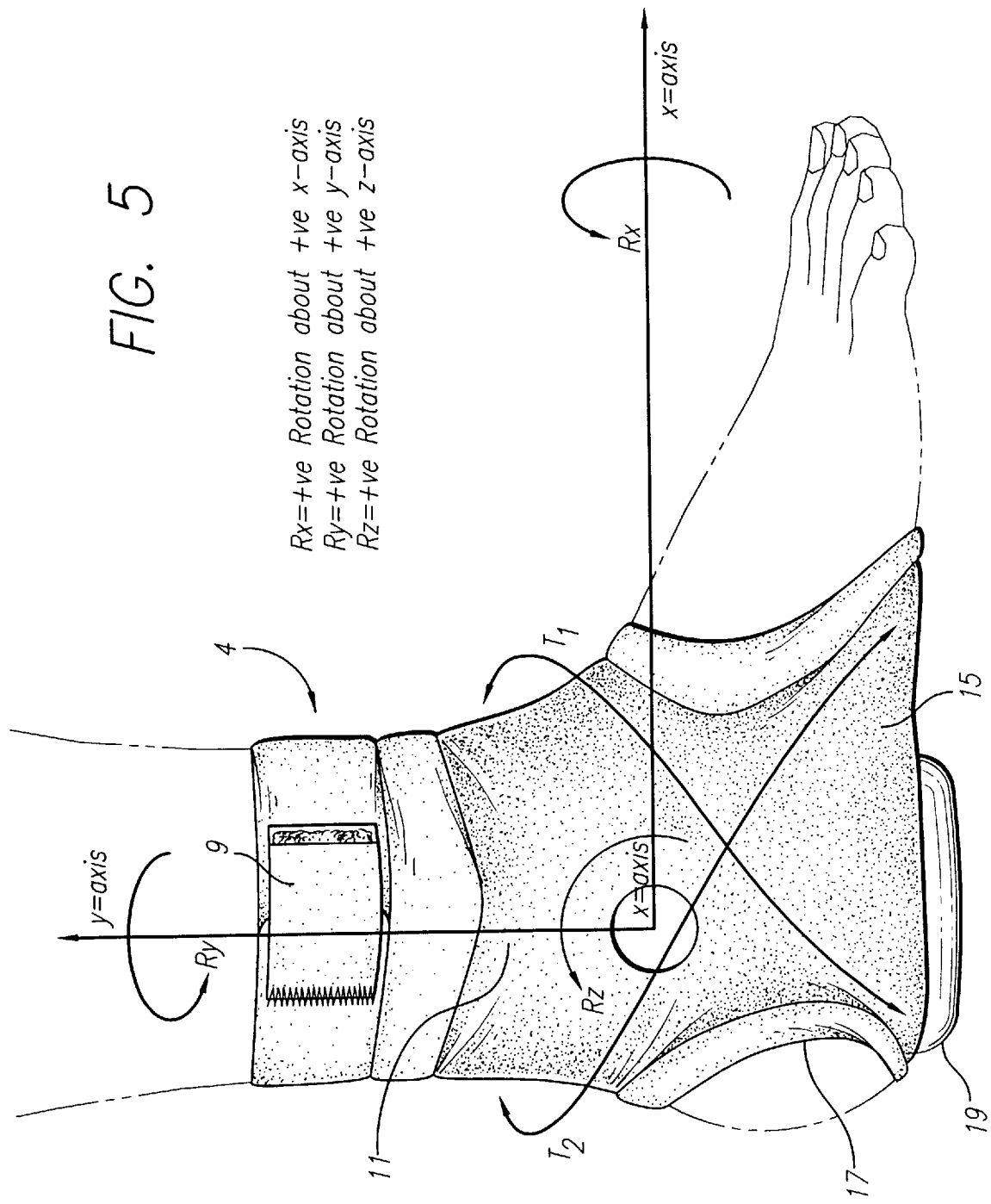

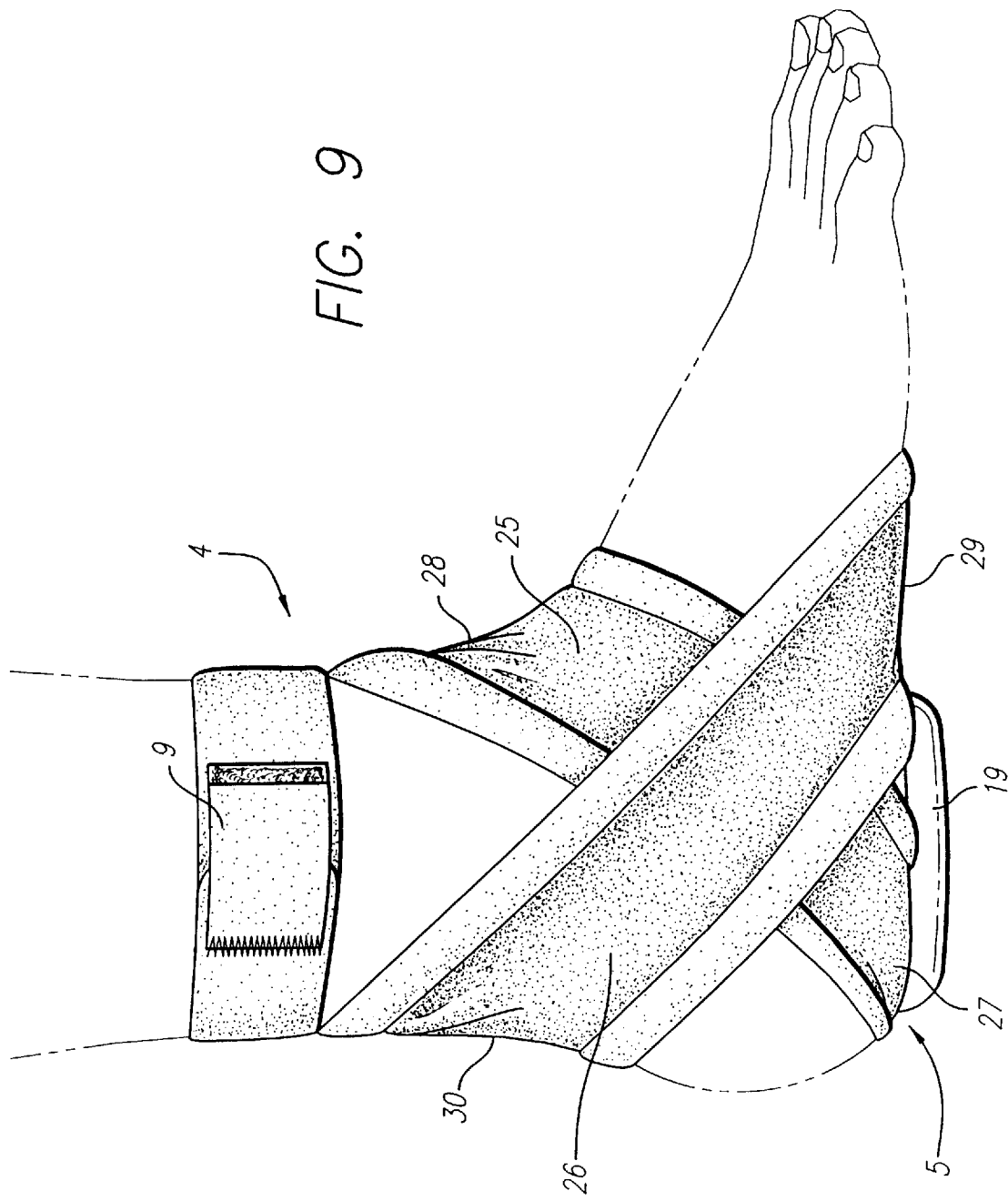

ANKLE BRACE

RELATED APPLICATIONS

This application is a continuation-in-part application of U.S. Ser. No. 08/773,412 filed Dec. 27, 1996, now abandoned.

TECHNICAL FIELD

The present invention relates to an ankle brace or splint.

Statistics suggest that there are three times as many ankle related injuries as there are knee related ones. Researching current splint types further suggests that there are far greater options for knees than there are for ankles (as seen in most catalogues). This lack of serious ankle splint options in conjunction with user dissatisfaction in their inability to live up to design expectations without compromising performance has led to the development of the present invention.

BACKGROUND ART

Summarized below are six different types of devices used for supporting, bracing and splinting ankles. A brief critique on each type is also provided in an attempt to bring to light their limitations. Orthotic type devices with rigid and semi-rigid moulded heel cups are not discussed here since they require specialized preparation, are not off the shelf products, and require—customized fitting. This type is also the most restrictive of athletic performance.

Type-1: All purpose elastic or neoprene wraps (long strips with hook and loop-type closure options)

This type is claimed to be a universal device which is used for applying compression to the effected area (the ankle in this case) by wrapping tightly. In the case of the neoprene it also provides thermal support. This type offers very little structural support and is both difficult and time consuming to apply. In cases of self application it is especially difficult if one suffers from injury pain and/or due to a lack of agility has limited reach. Tight wrapping may effect circulation. Any firmness in fit achieved is reduced significantly soon after use. It can become bulky (especially the neoprene straps) and there is no adjustment of fit possible once applied. They can become complicated since the tail end must come to rest at a certain point to complete closure (typically by hook and loop-type fasteners).

Type-2: Figure-eight elastic sock with open toe and heel.

This type is also for applying compression. They are simpler, less bulky and much easier and less time consuming to put on than Type-1. Once again it offers token structural support. The device is fixed for a given size and allows no provision to adjust or control the final fit. In cases where the user is experiencing pain in the region it is very difficult to put on and to take off. There are not enough device sizes to effectively fit the wide range of ankle/foot size variations. The device assumes that the foot is symmetric in geometry without complicated topography. This leads to uneven distribution of applied compressive pressure due to uneven stretching of the elastic.

Type-3: Neoprene or neoprene like material sock types with a variety of options. Some with open toes and/or heels, some with a zipper or hook and loop-type fasteners on the front or the side for easier access.

These are simple devices designed mainly to provide thermal support and some compression. They are softer and more comfortable than plain elastic, offer less compression and little structural support. With additional features they can become bulky. The devices are usually symmetrically prepared (assuming the lateral foot topography is identical to the interior) making them applicable to either the left or the right foot. Since this is not a realistic assumption an uneven distribution of compressive pressure is established. As in the previous case, most of these devices have no control features for achieving a desired final fit once applied. There are not enough device sizes to effectively fit the wide range of ankle/foot size variations. They are very difficult to put on and take off if the wearer suffers pain in the region (this includes the type with closures on the front or sides).

Type-4: Various Combinations of Types 2 and 3

This type of device provides a neoprene sock base onto which an elastic system is overlapped. It proposes a bulkier solution to the previous but with better control of final fit. The restraint provided is still very little and only compressive pressure onto the ankle region may be adjusted for. These devices suffer from identical limitations outlined in Types 2 and 3 above.

Type-5: Non stretch canvas or nylon or synthetic leather based braces with lace-up hook and loop-type fasteners and buckle combination frontal closure options and with thin plastic plate or flexible metal inserts.

These are currently claimed to be the most support providing splints in the market. Their potential of preventing injury and providing after injury support seems to be grossly overrated when the difficulties presented and their limitations imposed upon general performance are investigated.

They offer only passive restraint. They are heavy, bulky, very cumbersome and take a long time to put on. They require a fair degree of forcefulness to apply and if already injured and suffering pain then it is close to impossible to apply. Since they are made from non stretch materials, the splints are incapable of forming perfectly onto the lower leg, ankle and foot topography all at once. This produces uneven compression on the applied region. The plastic inserts are plate-like and incapable of perfectly forming to the region. The flexible metal inserts do little to provide stability. Both insert types and other typical rigid fixtures such as buckles and lace eyelets cause discomfort soon after application. In most cases, the base component onto which all other attachments are sewn on to are symmetrically cut and composed, once again wrongly assuming a symmetric foot topography. This fact further limits the effectiveness of the final fit. They appear not to facilitate any traction between the inner shoe and the outer splint surfaces since all outer surfaces are both shiny and slippery. They are complicated in design requiring many components and a wide range of specialised sewing processes to manufacture. They are expensive and not user friendly. All final fit adjustments must be made outside the shoe. In order to alter the fit, one must begin the lacing or hook and loop-type strapping process all over again. General performance is compromised for those using the splints as an injury prevention measure due to mainly the rigid nature of the designs and the inherent restrictions that they impose. The designs possess no reactive features that tend to recover the foot to the healing position when it experiences forced adverse movement such as inversion. Furthermore, even though the splints are tightly laced up or hook and loop-type strapping is applied tightly, there still appears to be some freedom of movement within the splint. There is only token traction between the outer ankle/foot and the inner splint surfaces to stop local movement from taking place. General professional feedback perceives this type to be ineffective and totally awkward.

Type-6: Traditional taping by skilled trainers, sports conditioners and physiotherapists.

Perceived generally by athletes to be the most effective for protection and prevention purposes. There is less slippage experienced. It takes extremely long to apply. One must be a trained professional to apply it correctly. It cannot be self applied effectively due to the reach factor. There needs to be good communication between the applier and the user for continuous adjustment during application. Further corrective adjustments cannot be made once application is completed. New strapping tapes must be used every time. Even though individual tapes are inexpensive, when one considers accumulated costs over time of the tapes and the time of a paid trainer who applies it, then the costs become very significant very quickly. Taping provides only passive restraint. The effect of such restraint is reduced dramatically after only a short period of exercise leading to increased play and possibly becoming slippery inside the shoe.

The present invention seeks to overcome or least ameliorate the problems and disadvantages of the prior art outlined above.

DISCLOSURE OF THE INVENTION

The invention provides a totally new solution to the problem of general ankle splinting. Its unique design successfully combines simplicity with serious ability to protect and actively support lateral ligaments without hindering performance. It does so by, in its preferred form, actively restraining the foot in the correct healing position at all times in relation to the ankle.

According to one aspect, the present invention provides an ankle brace adapted for fitting to an ankle comprising:

ankle anchor means adapted to attach to the ankle of a user above the ankle joint;

heel support means adapted to fit under and support the heel of the user;

first bracing means extending from a point at or adjacent to a rearward lateral portion of the heel support means to a point at or adjacent a forward lateral portion of the ankle anchor means when the ankle brace is fitted to the foot of said user;

second bracing means extending from a point at or adjacent to a forward lateral portion of the heel support means to a point at or adjacent a rearward lateral portion of the ankle anchor means when the ankle brace is fitted to the foot of said user;

said first and second bracing means each being resilient and extending around a lateral side of the user's ankle in use and each adapted, in use, to apply a tensile force to the heel support means so as to seek to raise the lateral side of the user's heel and resist inversion of the ankle.

Preferably, said first and second bracing means comprise resilient straps. For preference, said straps are adjustable in length to allow for variations in foot size. Preferably, said straps are formed of resilient plastics material, such as neoprene. For preference, the ankle anchor means is attached on the inner side of the user's heel to the heel support means. In a preferred form, the components of the brace are integrally formed from a single piece of resilient material. The resilient material may, for preference, be formed as a laminate of different materials. Preferably, the ankle anchor means includes adjustable straps which wrap around the user's leg in use to provide said attachment above the ankle joint. For preference, said first and second bracing means are provided by a single piece of material having a Y-shaped configuration, the base of the Y being attached to the heel support means and the ends of the Y yoke wrapping around the upper ankle to form the ankle anchor means. The ends of the Y yoke are preferably provided with complementary hook and loop type fasteners to provide adjustable attachment to one another.

In a further preferred form, the heel support portion is provided with a generally boomerang shaped cushioning element or pad extending generally across the middle of the heel support portion and partly along the outer side of the heel supporting portion towards the rear portion of the heel support. The pad may be integrally formed with the heel supporting means or fixedly or removably attached thereto. For preference, the heel supporting means is shaped at its rear portion to form a raised cup-like edge into which the rear of the user's heel fits during use.

The splint/brace in its preferred form is not a symmetric design. For simplicity only the right splint/brace will be considered in all following discussions and references. The left splint/brace design is simply the mirror image of the right.

BRIEF DESCRIPTION OF DRAWINGS

A preferred embodiment of the present invention will now be described, by way of example only, with reference to the accompanying drawings, in which:

FIGS. 4a–4c show a lateral side, inner side and bottom view of the applied brace, respectively;

FIG. 5 shows a side elevation of the brace fitted to a user and the tensional forces applied by the brace;

FIG. 9 shows a lateral side view of an alternate embodiment of the brace applied to the ankle.

DETAILED DESCRIPTION

A discussion regarding the splint/brace design features and application guidelines are presented in the respective sections that follow.

Figure 3:
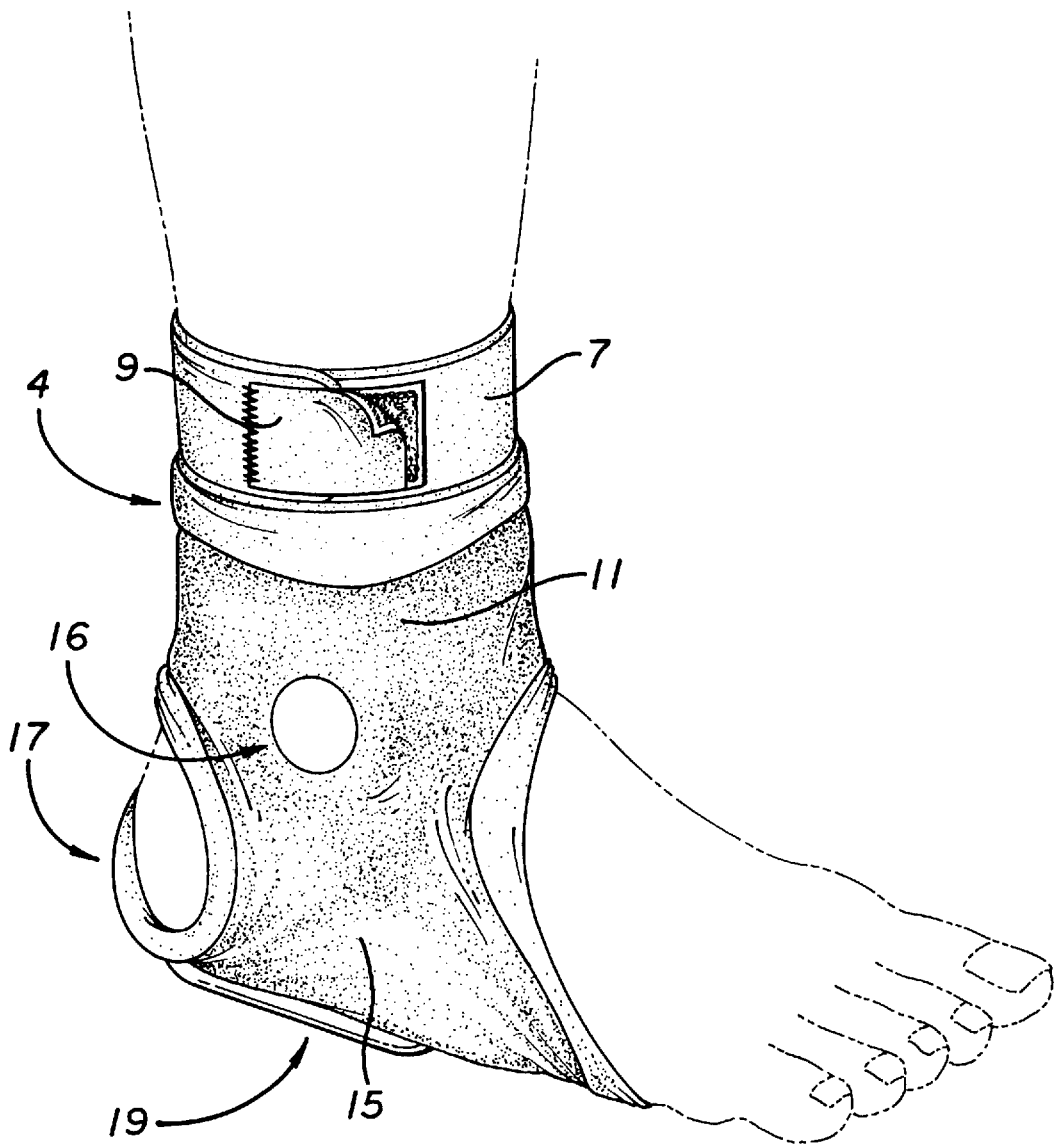
FIG. 3 shows a perspective view of the brace of FIG. 1 when applied to the ankle.
Figure 4A:
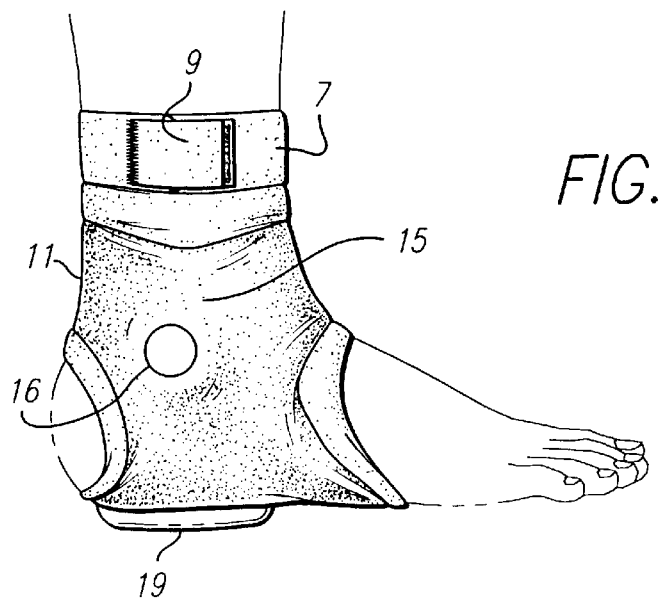
Figure 4B:
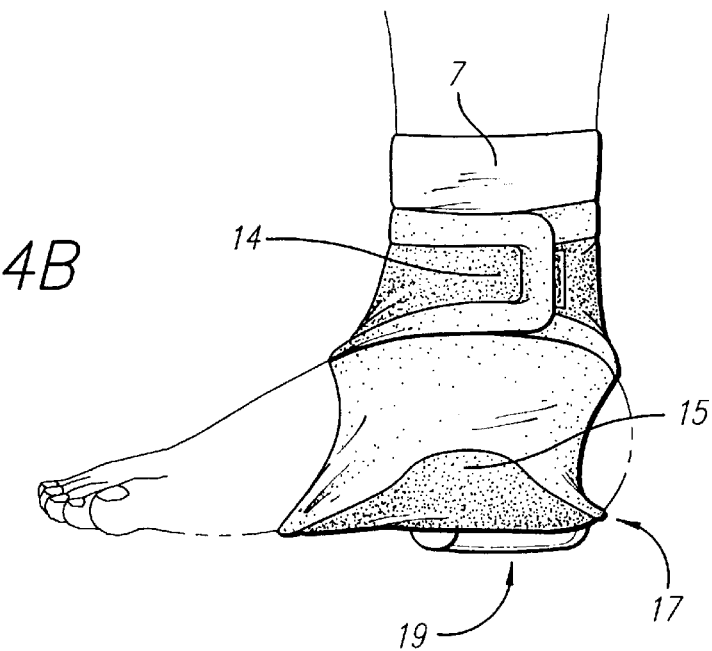
Figure 4B:
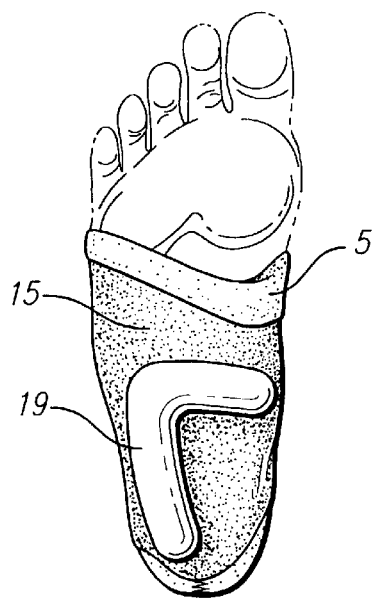

Referring to the drawings, the brace consists of a one piece construction having a number of portions. The brace is preferably formed of a resilient plastics material, in this embodiment neoprene {poly(2-chloro-1,3-butadiene)]} as it highly resilient, has high tensile strength and provides hard-wearing qualities, however, other rubber-like materials could be used. The brace consists of a central heel supporting portion 5 having extending therefrom, on one side, via a reduced width bridge portion 6, an inner strap portion 7 which is adapted in use to wrap around the upper ankle 4 of the user to provide a fixed anchor point for support of the heel supporting portion 5, as best shown in FIGS. 3 and 4. The inner strap 7 in conjunction with the bridge portion 6 is generally T-shaped with the cross or lateral portion 8 having complementary adjustable hook and loop-type fasteners 9 and 10 at each end and being dimensioned to enable the cross portion 8 to wrap around the upper ankle 4 of the user and be fastened on the outer side of the ankle as best shown in FIG. 4.

Figure 2:
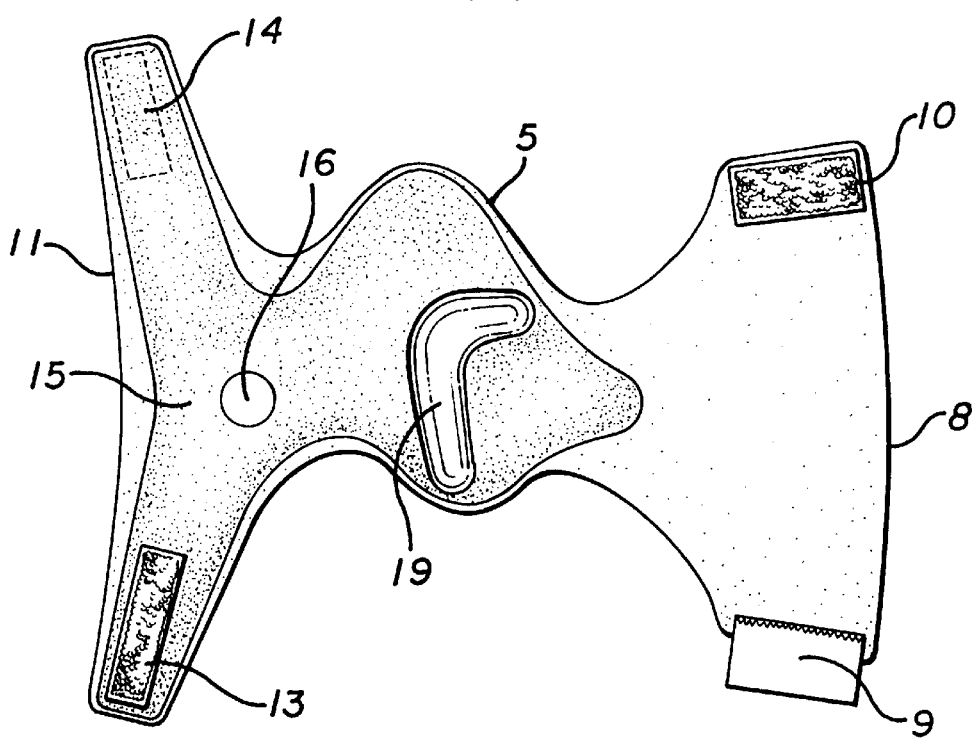
FIG. 2 shows an underside view of the brace of FIG. 1.

Extending from the other side of the heel supporting portion 5 is outer strap portion 11. Again this strap portion 11 is generally Y or T-shaped in configuration with the cross or lateral portion 12 having complementary adjustable hook and loop-type fasteners 13 and 14 at each end. This outer strap portion 11 is provided with an outer layer of resilient material 15, preferably MELCO T5500™, which is adhered to the material forming the strap portion 11. This outer layer 15 preferably extends under the heel support region as best shown in FIG. 2. A cutout 16 is provided in the outer layer 15 adjacent the protruding ankle bone to relieve direct pressure on the ankle.

The heel support portion 5 is shaped at its rear edge to form a cup formation 17 into which the rear of the user's heel fits to prevent rearward sliding of the heel in the brace, as shown in FIGS. 3 and 4. The inner side of the heel support portion may also be provided with a layer 18 of MELCO T5500™ adhered thereto, as shown in FIG. 1, to assist gripping of the user's foot.

The heel support portion 5 is provided with a generally boomerang shaped cushioning element or pad 19 extending across the center of the heel support portion 5 and partly along the outer side of the heel supporting portion 5 towards the rear portion of the heel support 5.

The main outstanding features contributing to the uniqueness of the splint/brace are its in-built dynamic response to adverse movement, boomerang-shaped heel pad 19, its streamlined and uncomplicated form, its simplicity and user friendliness. It provides protection during both the swing phase of the gait cycle and the stance phase without compromising performance. All design objectives have been met efficiently as outlined by the following passages.

Figure 1:
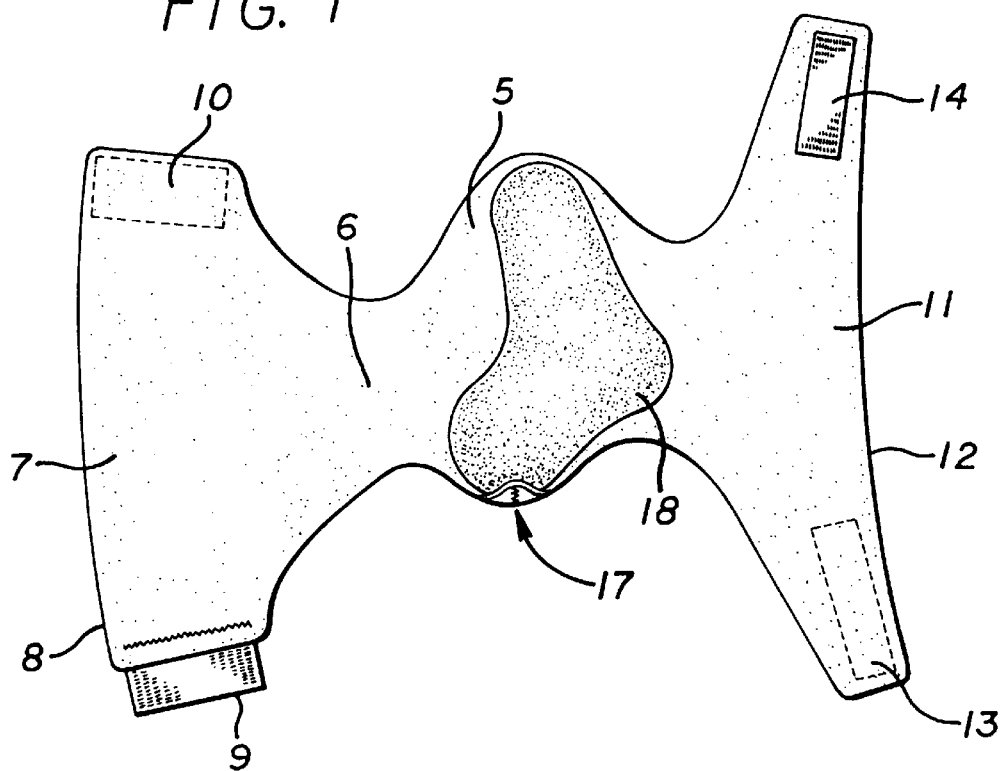
FIG. 1 shows a plan view of the brace according to one embodiment of the invention.

The brace is preferably constructed from 3 mm thick neoprene laminated with nylon fabric on both sides and MELCO T5500™, as best shown in FIGS. 1 and 2. T5500™ is a tough, adhesive backed material which has nylon mesh reinforcement and acrylic dimples that provide excellent resilience and grip respectively. The T5500™ component is strategically shaped and is applied (by a heat press) to provide maximum resilience in aid of the lateral ligaments and maximum traction. The boomerang-shaped heel pad 19 is silicon based and all strap closures 9, 10, 13 and 14 are typically achieved using hook and loop-type fasteners, for example, such fasteners as marketed under the registered trademark VELCRO®.

The brace is a dynamically active brace. A high degree of tension is maintained in outer strap portion 11 (see FIG. 3) upon proper application, with the foot restrained in the correct healing position. When the foot is forced towards a position other than the healing one, an increase in the level of overall tension is consequently experienced in the outer strap portion 11, as best shown in FIG. 5. In turn an immediate resistance is triggered opposite to the direction of the foot proportional in magnitude to the adverse force, in aid of the lateral ligaments. This applies to internal inversions of the foot and extreme pitching of the foot up or down. It is the approximate bi-axial coupling of the two separate tensions, T1 and T2 (see FIG. 5 for a detailed explanation) in outer strap portion 11 that help achieve the necessary overall stability during general performance and resistance against any adverse movement.

Referring to FIG. 5, the action of the tensions T1 and T2 can be explained as follows, assuming that perfect traction exists between the surface of the brace and the sole of the user's foot and that the brace is correctly applied with the outer strap 11 already in tension. A forced Rx (where Rx=+ve rotation about+ve x-axis) causes inward inversion which is countered by a proportionate increase in both T1 and T2. A forced Rz (where Rz=+ve rotation about+ve z-axis) causes pitching up of the foot (dorsiflexion) which is countered by a proportionate increase in T1 (with a decrease in T2). A forced negative Rz causes pitching down of the foot which is countered by a proportionate increase in T2 (with a decrease in T1). A forced Ry (where Ry=+ve rotation about+ve y-axis) causes inward twisting of the foot in the z and x plane which is countered by a proportionate increase in T2 (with a decrease in T1). A forced negative Ry causes outward twisting of the foot which is countered by a proportionate increase in T1 (with a decrease in T2).

The splint/brace also helps provide torsional stability. Much of these traits are attributable to the excellent traction that exists between the foot (with or without sock 22) and the inner surface of the splint and between the outer surface of splint and the inner surface of the shoe 21.

The unique boomerang-shaped heel pad 19 is designed to help achieve the healing position during the stance phase by passively loading the ankle joint into valgus and dorsiflexion. A soft 3D silicon based design for the boomerang-shaped heel pad is provided which is contoured for maximum effect. This pad 19 may be adhered onto the splint to render it a single piece design or made available in the packaging of the splint as a separate piece that may both complement the splint or be used on its own in less severe situations. The two piece option gives the user the freedom of choice to adjust its placement in the shoe or to remove it totally if there is any discomfort experienced. The two piece option does not compromise the effectiveness of the design.

The heel pad also offers the additional benefit to an essential movement in sport not previously addressed. The benefit applies to rapid sideways motion such as side-stepping in basketball and football, and cross-court as in tennis. The heel pad causes negative inversion of the ankle during normal stance thus, when the foot pushes off during sideways movement, the foot experiences minimal inversion and tension is minimised in the lateral ligament complex. The foot is effectively pushing off a plane that is inclined to the ground and thus sideways movement can be carried out with more efficiency and minimal risk of injury.

Referring to FIGS. 8a to 8e detailed views of one embodiment of the heel pad according to one embodiment the invention are shown. The drawings show a pad for the right ankle and a similar shape would be used for the left ankle though in mirror image. This form of the pad is larger than that described earlier and fits around the rear of the heel to cup and support it. As can be seen from the drawings the heel pad is generally acuate in shape when viewed in plan and from the front or rear. It has a raised side wall 23 and rear portion 24 to cup the user's heel.

Referring to FIG. 9, an alternate embodiment of the invention is shown. In this embodiment rather than having an integral Y-shaped strapping to provide tensions T1 and T2 (see FIG. 5), the outer strap portion 11 comprises a pair of criss-crossing straps 25 and 26 extending from the lateral side of the heel support 5. The remainder of the brace is the same as that shown in the other embodiments. Strap 25 extends from the rearward lateral portion 27 of the heel support 5 to a forward lateral portion 28 of the ankle anchor 8. Strap 26 extends from the forward lateral portion 29 of the heel support-5 to a rearward lateral portion 30 of the ankle anchor 8. The free ends of the straps 25 and 26 can be provided with hook and loop type fasteners 13 and 14 respectively, in a similar manner to strap 15 (see FIG. 4b)

which wrap around above the ankle and fasten on the medial side of the foot.

The splint according to a preferred form of the invention is an active splint that offers an immediate and proportional resistance to forced movement of the ankle/foot away from the healing position. This correctly supports the ankle during the swing phase.

The unique boomerang-shaped heel pad 19 mechanically loads the ankle joint into valgus and dorsiflexion during the stance phase.

The adoption of the splint does not restrict performance but its effect is maintained.

The high front cut design further offers unrestricted up and down foot movement.

The splint offers a left and a right foot option since it is purpose designed and therefore is not symmetric in design.

It offers uniform compression to the ankle region, particularly when it is worn inside a shoe. Compression may be adjusted by manipulating the closure of straps 7 and 11.

It provides thermal support through the insulation of body heat.

It is comfortable to wear without any rigid protruding components or inserts and becomes unnoticeable soon after application.

It offers a soft exterior design with no exposed hook and loop-type fasteners, buckle or lace eyelets. All hook and loop components are well covered.

Excellent traction is provided for the frictional interaction between two crucial sets of surfaces. The first is between the foot (with or without sock) and the inner splint/brace surfaces. The second is between the outer splint and inner shoe surfaces. The grip is maintained even when these surfaces are wet.

It can be self applied, adjusted and removed with great ease and speed without requiring aid from a second party.

It is not cumbersome to apply in that there are no passages for the foot to be forced through.

It can be worn under shin guards.

All adjustments may be made without taking the shoe off or unlacing.

The boomerang-shaped heel pad 19 in conjunction with the neoprene base help cushion the heel from ground impact and during stance.

It is lightweight and streamlined in design.

Its features can be incorporated into general athletic shoe design.

The splint/brace is user friendly, particularly to those suffering pain.

It is washable.

It can be applied both inside and outside a sock 22. In the case of outside sock application, the sock 22 offers better ventilation and moisture absorption.

The splint/brace is inexpensive to manufacture and utilises minimum components.

Now described below are the steps for application of the splint/brace. Here all guidelines and illustrations are once again related to only single piece, right foot splint application while sitting. The following steps provide single piece splint/brace design in shoe application guidelines:

Step 1 Orientate the device so that the slightly raised heel cup 17 is nearer to the body with the boomerang heel pad 19 beneath. This places the inner and outer strap portions 7 and 11 to the left and right respectively as shown in FIG. 1.

Step 2 Having already relieved the lacing on the shoe 21 place the brace inside and position correctly.

Step 3 Place the foot 20 into the shoe 21 and rest its weight on the open splint/brace.

Figure 6:
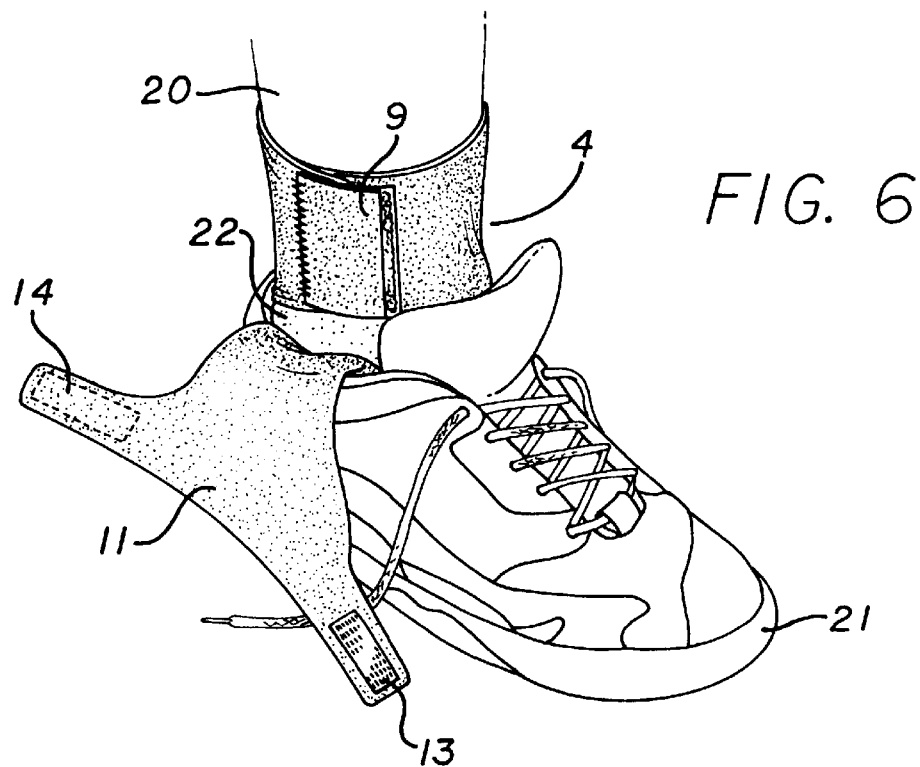
FIG. 6 shows a lateral perspective view of the brace in an in-shoe application.

Step 4 Proceed to apply inner strap 7 without causing excessive tension in the vertical direction. Achieve a firm and comfortable fit by completing the closure of strap 7 ends on the lateral side. See FIG. 6.

Step 5 Hold the outer resilient strap 11 with both hands and pull forcefully up towards the knee producing an outer inversion and dorsiflexion, thus achieving the necessary healing position.

Figure 7:
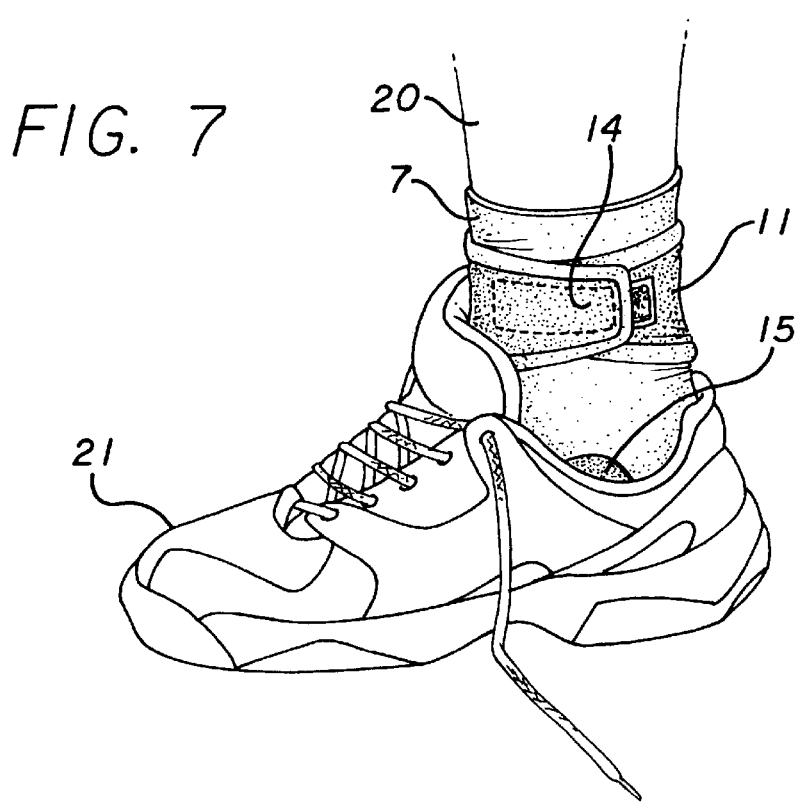
FIG. 7 shows an inner perspective view of the in-shoe application of FIG. 6.
Figure 8E:
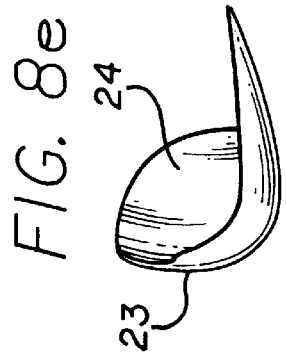
FIGS. 8a–8e show plan, front, underside, left side and right side views respectively, of a heel support pad in accordance with the invention.
Figure 8A:
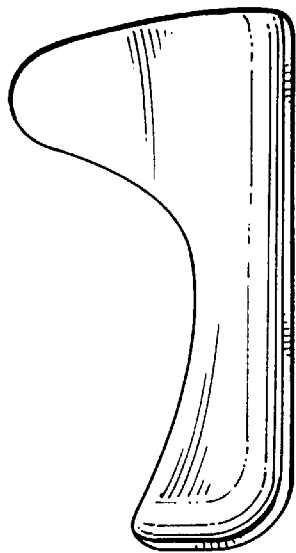
Figure 8B:
Figure 8C:
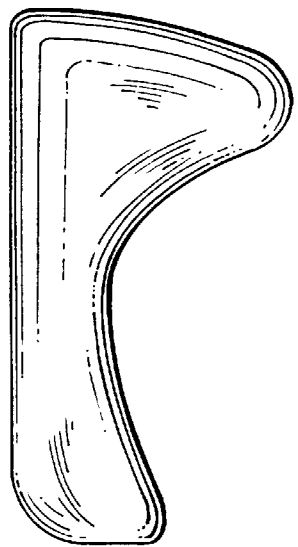
Figure 8D:
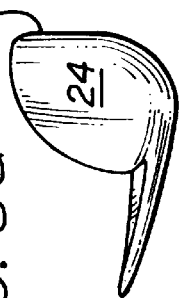

Step 6 While still maintaining the tension in outer strap 11 and the correct healing position proceed to wrap and achieve closure of the ends of outer strap 11. See FIG. 7.

Step 7 Lace up the shoe 21 and hence complete the brace/splint in shoe application.

For out-of shoes application of the splint proceed as follows:

Step 1 Orientate the device so that the slightly raised heel cup 17 is nearer to the body with the boomerang heel pad beneath. This places straps 7 and 11 to the left and right respectively as shown in FIG. 1.

Step 2 Position the splint onto the ground while maintaining the above orientation.

Step 3 Correctly position the foot on to the open splint beneath and rest with full weight upon it.

Step 4 Proceed to apply inner strap 7 without causing excessive tension in the vertical direction. Achieve a firm and comfortable fit by completing the closure of strap 7 ends on the lateral side.

Step 5 Hold the outer resilient strap 11 with both hands and pull forcefully up towards the knee producing an outer inversion and dorsiflexion, while still maintaining the weight.

Step 6 While still maintaining the tension in strap 11 and the correct healing position proceed to wrap and achieve closure of the ends of strap 11. See FIG. 4(*b*), hence completing the application.

It should be noted that the two piece splint design with an unattached boomerang heel pad 19 may only be applied inside a shoe 21. In this case the heel pad component 19 must be placed and positioned inside the shoe 21 prior to the placement of the splint component. The normal steps may then be taken.

In the cases of both single and two piece left foot splint designs, all given application guidelines are simply mirrored.

It will be appreciated that further embodiments and exemplifications of the invention are possible without departing from the spirit or scope of the invention described.

We claim:

1. An ankle brace adapted for fitting to an ankle comprising:

ankle anchor means adapted to attach to the ankle of a user above the ankle joint;

heel support means adapted to fit under and support the heel of the user;

first bracing means extending from a point at or adjacent to a rearward lateral portion of the heel support means to a point at or adjacent a forward lateral portion of the ankle anchor means when the ankle brace is fitted to the foot of said user;

second bracing means extending from a point at or adjacent to a forward lateral portion of the heel support means to a point at or adjacent a rearward lateral portion of the ankle anchor means when the ankle brace is fitted to the foot of said user;

said first and second bracing means each being resilient and extending around a lateral side of the user's ankle in use and each adapted, in use, to apply a tensile force to the heel support means so as to seek to raise the lateral side of the user's heel and resist inversion of the ankle.

2. An ankle brace according to claim 1 wherein said first and second bracing means comprise resilient straps.

3. An ankle brace according to claim 2 wherein said straps are adjustable in length to allow for variations in foot size.

4. An ankle brace according to claim 1 wherein said straps are formed of resilient plastics material.

5. An ankle brace according to claim 1 wherein the ankle anchor means is attached to a medial side of heel support means.

6. An ankle brace according to claim 1 wherein the heel support means and the first and second bracing means are integrally formed from a single piece of resilient material.

7. An ankle brace according to claim 6 wherein the resilient material is formed as a laminate of different materials.

8. An ankle brace according to claim 1 wherein the ankle anchor means includes adjustable straps which wrap around the user's leg in use to provide said attachment above the ankle joint.

9. An ankle brace according to claim 1 wherein both said first and second bracing means are provided by a single piece of material having a Y-shaped configuration, the base of the Y being attached to the heel support means and the ends of the Y yoke wrapping around the upper ankle to form the ankle anchor means.

10. An ankle brace according to claim 9 wherein the ends of the Y yoke are provided with complementary hook and loop fasteners to provide adjustable attachment to one another.

11. An ankle brace according to claim 1 wherein the heel support means is provided with a generally boomerang shaped cushioning element or pad extending generally across the middle of the heel support means and partly along the lateral side of the heel support means towards the rearward portion of the heel support means.

12. An ankle brace according to claim 11 wherein the pad is integrally formed with the heel support means.

13. An ankle brace according to claim 1 wherein the heel support means is shaped at its rearward portion to form a raised edge into which the rear of the user's heel fits during use.

14. A method of bracing an ankle comprising fitting an ankle brace, according to any one of the preceding claims, to the ankle such that a tensile force is applied to the heel support means so as to seek to raise the lateral side of the user's heel.

15. A heel pad for use in the brace according to any one of the preceding claims comprising a generally boomerang shaped cushioning element or pad when viewed from front or rear relative to the user's foot having an upwardly extending side and rear wall and base support portion upwardly inclined towards an edge remote from said raised side.

* * * * *